United States Patent
Lee et al.

(10) Patent No.: US 6,316,265 B1
(45) Date of Patent: *Nov. 13, 2001

(54) DETERMINATION OF % GLYCATED HEMOGLOBIN

(75) Inventors: Evelyn Mok Lee, Skokie; David A. Westerberg, Grayslake; Haiou H. Yao, Libertyville; Janina Adamczyk, Gurnee; Melissa A. Christensen, Palatine, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,219

(22) Filed: Sep. 17, 1999

Related U.S. Application Data

(63) Continuation-in-part of application No. 08/816,237, filed on Mar. 13, 1997, now Pat. No. 6,162,645.

(51) Int. Cl.[7] .................................................. G01N 33/72
(52) U.S. Cl. .............................. 436/67; 436/66; 436/164; 436/172; 436/805; 436/824; 436/518; 436/524; 435/7.1; 435/960
(58) Field of Search ............................... 436/56, 57, 63, 436/66, 67, 87, 164, 166, 172, 175, 805, 824, 501, 518, 524, 526, 527, 536, 542; 435/2, 7.1, 960, 961, 968

(56) References Cited

U.S. PATENT DOCUMENTS

| | | | |
|---|---|---|---|
| 4,269,605 | 5/1981 | Dean et al. | 436/67 |
| 4,496,722 | 1/1985 | Gallop et al. | 544/69 |
| 4,727,036 | 2/1988 | Knowles et al. | 436/547 |
| 4,861,728 | 8/1989 | Wagner | 436/501 |
| 5,045,234 | 9/1991 | Bonicolini et al. | 252/408.1 |
| 5,110,745 | 5/1992 | Kricka et al. | 436/87 |
| 5,206,144 | 4/1993 | Zeuthen et al. | 435/7.25 |

(List continued on next page.)

FOREIGN PATENT DOCUMENTS

| | | |
|---|---|---|
| 292 443 | 11/1988 | (EP) . |
| 455 225 | 11/1991 | (EP) . |
| 708 337 | 4/1996 | (EP) . |
| 6307558 | 4/1988 | (JP) . |
| 3244360 | 11/1991 | (JP) . |
| 4109163 | 4/1992 | (JP) . |
| 4145367 | 5/1992 | (JP) . |
| 90/06516 | 6/1990 | (WO) . |
| 90/13818 | 11/1990 | (WO) . |
| 92/22818 | 12/1992 | (WO) . |
| 93/18407 | 9/1993 | (WO) . |
| 98/40750 | 9/1998 | (WO) . |

OTHER PUBLICATIONS

D.E. Goldstein et al., "Glycated Hemoglobin: Methodologies and Clinical Applications", *Clin Chem*, vol. 32 (1986): pp. B64–B70.

*Primary Examiner*—Maureen M. Wallenhorst
(74) *Attorney, Agent, or Firm*—Regina M. Anderson

(57) ABSTRACT

A glycated hemoglobin assay utilizes a simple procedure for the determination of standardized %GHb in whole blood samples correlated to the Diabetes Control and Complications Trial (DCCT). First, a lysed whole blood sample is incubated with a solid phase that is coupled with boronic acid or similar boronate compound through covalent linkage chemistries known in the art. Next, a labeled antibody to human hemoglobin is added and the resulting signal is directly proportional to the %GHb in the sample. The advantages of measuring %GHb using a single determination include high precision and, since the assay is easily automatable, high throughput. With automation, this assay can also be consolidated with other testing on one analyzer. The method according to the various embodiments of the invention thus eliminates the need for two measurements: one for GHb and another for total hemoglobin (THb).

10 Claims, 17 Drawing Sheets

U.S. PATENT DOCUMENTS

| | | | |
|---|---|---|---|
| 5,242,842 | 9/1993 | Sundrehagen | 436/536 |
| 5,284,777 | 2/1994 | Rosenthal et al. | 436/518 |
| 5,294,336 | 3/1994 | Mizuno et al. | 210/198.2 |
| 5,348,649 | 9/1994 | Mizuno et al. | 210/198.2 |
| 5,468,646 | 11/1995 | Mattingly et al. | 436/501 |
| 5,470,759 | 11/1995 | Sugiyama et al. | 436/541 |
| 5,478,754 | 12/1995 | Brandt et al. | 436/518 |
| 5,506,114 | 4/1996 | Sangha | 435/15 |
| 5,506,144 | 4/1996 | Sundrehagen | 436/66 |
| 5,543,524 | 8/1996 | Mattingly et al. | 546/104 |
| 5,589,393 | 12/1996 | Fiechtner et al. | 436/15 |
| 6,162,645 * | 12/2000 | Lee et al. | 436/67 |

* cited by examiner

DETERMINATION OF % GLYCATED HEMOGLOBIN

This application is a continuation-in-part of application Ser. No. 08/816,237, filed on Mar. 13, 1997 and now U.S. Pat. No. 6,162,645, issued on Dec. 19, 2000.

FIELD OF THE INVENTION

The present invention relates to a method for detecting the presence or amount of glycated hemoglobin (GHb) in a blood sample, and more particularly, to an improved, highly accurate, one-read method for assessing percentage glycated hemoglobin, that is, a method which does not require a measurement of total hemoglobin (THb).

BACKGROUND OF THE INVENTION

Glycated hemoglobin (GHb) refers to a series of minor hemoglobin components that are formed via the attachment of various sugars (most commonly glucose) to the hemoglobin molecule. The human erythrocyte is freely permeable to glucose. Within each erythrocyte, GHb is formed at a rate that is directly proportional to the ambient glucose concentration. The reaction of glucose with hemoglobin is nonenzymatic, irreversible and slow, so that only a fraction of the total hemoglobin is glycated during the life span of an erythrocyte (120 days). As a result, the measurement of GHb provides a weighted "moving" average of blood glucose levels that can be used to monitor long-term blood glucose levels, providing an accurate index of the mean blood glucose concentration over the preceding 2 to 3 months. The most important clinical application of this is in the assessment of glycemic control in a diabetic patient.

Hemoglobin A1c (HbA1c) is one specific type of glycated hemoglobin and is the most important hemoglobin species with respect to diabetes. The amount of total hemoglobin that is HbA1c is approximately 3 to 6% in nondiabetics, and 20% or greater in diabetes that is poorly controlled (Goldstein DE, et al, Clin Chem 32: B64-B70 (1986)). In HbA1c, glucose is attached to the amino terminal valine residue of one or both of the hemoglobin A beta chains. HbA1c (as well as other glycated Hemoglobin A1 species) can be separated from nonglycated hemoglobins by methods that separate molecules based on differences in their electrical charges. Glycation of hemoglobin also occurs at other sites on the hemoglobin molecule, but these species cannot be separated from nonglycated hemoglobins based on charge differences, so all of these species of hemoglobin are termed HbA0. Methods that measure all forms of glycated hemoglobin are said to measure total GHb. Since glycation at one site appears to be proportional to glycation at any other site, there is a linear relationship between GHb and HbA1c. The Diabetes Control and Complications Trial (DCCT) Research Group reported that a 1% change in GHb (%HbA1c) represents an average change of 300 mg/L in blood glucose levels over the preceding 120 days.

Traditional methods of assessing blood glucose control in diabetes, including urine and blood glucose levels, have a limited value since they can fluctuate, do not provide information on glucose levels over time, and are influenced dramatically by diet. However, measurement of GHb is an accurate index of a person's mean blood glucose level over the preceding 2 to 3 months and can provide a diabetic patient an overview of their success in meeting long-term goals for controlling their blood glucose levels. Since GHb levels can be used to monitor a patient's glycemic control over time, a high degree of long-term assay precision and standardization across different methodology is essential. In response to these clinical requirements, the American Association of Clinical Chemistry (AACC) formed a subcommittee on GHb standardization in 1993. The GHb Standardization Subcommittee recommended that within-laboratory, between-run CVs be maintained at 5% or lower for all GHb assays, and that standardization be based on correlation to the DCCT for fresh samples. All manufactured assays must meet these requirements to receive certification.

Clinical assay methods separate GHb from total hemoglobin based on either charge differences or structural characteristics. Methods based on charge differences include cation exchange chromatography and electrophoresis, and separate HbA1 or HbA1c from HbA0 based on the difference in their charges. Ion exchange chromatography can be performed either in large columns, mini or micro columns, or by high pressure liquid chromatography (HPLC). Large column methods are impractical for routine use in a clinical laboratory, but simplified mini or micro columns are available. However these methods show poor reproducibility and are very sensitive to variations in temperature, pH and ionic strength. While electrophoretic methods are not as sensitive to temperature, pH or ionic strength, they have other drawbacks which are also seen with ion exchange methods, namely, interference by a labile GHb intermediate, which must be removed prior to GHb testing, problems if a hemoglobinopathy is present, sensitivity to sample storage conditions and interference from extraneous clinical factors, such as aspirin therapy, ethanol levels and uremia. Also, HPLC and electrophoresis require specialized equipment.

Methods based on structural characteristics include affinity binding or chromatography and immunoassays. These methods are less sensitive to small variations in temperature, pH or ionic strength, and generally are not affected by labile GHb intermediates, hemoglobinopathies or sample storage conditions or the extraneous clinical factors mentioned above. However these methods either involve separation of GHb from nonglycated components or require 2 separate determinations—one for total hemoglobin and a second for GHb or HbA1c—to calculate %GHb. Use of a boronate ligand coupled to a solid phase matrix can be used in affinity binding assays due to the affinity of boronate for GHb. Ratios of bound (glycated) to nonbound (nonglycated) hemoglobin can then be quantified. Immunoassays measure HbA1c using HbA1c specific antibodies, but require 2 separate determinations, one for total hemoglobin and the other for HbA1c, in order to calculate %GHb. Alternatively an immunoassay may bind all hemoglobin species using passive adsorption, then detect HbA1c with a specific antibody conjugate; however this method may be adversely affected by hemoglobin variants.

What is therefore needed in the art is an improved, highly accurate method of detecting the presence or amount of glycated hemoglobin in a blood sample which does not require a determination of the total hemoglobin content as well.

SUMMARY OF THE INVENTION

The unique and novel approach described herein measures %GHb in whole blood samples and provides a %GHb result following only a single measurement. This differs from the methods described above and currently available in the art which require separate total and GHb measurements to calculate a %GHb result as, for example, a ratio of GHb/THb×100. The GHb assay described herein uses a simple procedure for the determination of DCCT Standardized %GHb in whole blood samples. First, a lysed whole blood sample is incubated with a solid phase that is coupled with boronic, phenylboronic or boric acid or related boronate compound through covalent linkage chemistries known in the art. This solid phase is novel since it specifically captures GHb in direct proportion to the %GHb in the sample. Next, a labeled component that recognizes human hemoglobin is added and the resulting signal is directly proportional to the %GHb in the sample. The advantages of measuring %GHb using a single determination include high precision (less than about 5% CVs) and, since the assay is easily automatable, high throughput (100 to 200 tests/hour). With automation, this assay can also be consolidated with other testing on one analyzer.

DETAILED DESCRIPTION OF THE PREFERRED EMBODIMENTS

Figure 1:
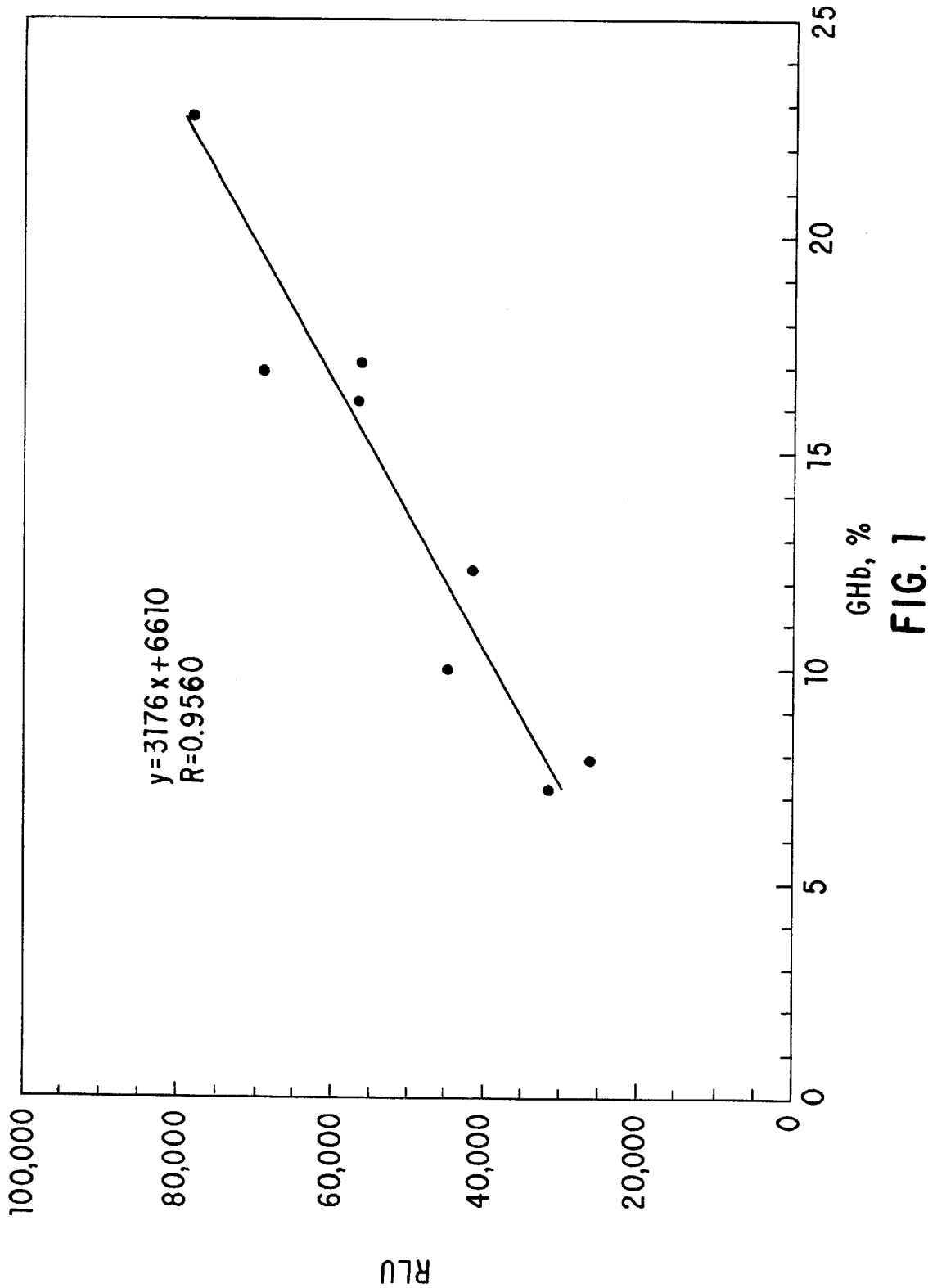
FIG. 1 is a graph illustrating the results of testing whole blood samples to determine %GHb levels using CMA/Merquat coated particles and samples pre-mixed with polyanion reagent according to one embodiment of the invention.

Per cent glycated hemoglobin (%GHb) is determined following hemolysis of the red blood cells in whole blood to release hemoglobin, after which samples are diluted and incubated with a solid phase having a boronate reactive group to which glycated hemoglobin binds. Subsequently, or simultaneously, the sample mixture is reacted with a labeled anti-hemoglobin Ab. The resulting signal is detected and is directly proportional to the %GHb in the sample. The method according to the various embodiments of the invention thus eliminates the need for two measurements: one for GHb and another for total hemoglobin, with a ratio to then determine % GHb.

Without being limited to any one particular theory, it appears that glycated hemoglobin binds to the boronate affinity complex attached to the solid phase. Nonglycated hemoglobin may compete directly with glycated hemoglobin for binding to the solid phase and thereby permit the accurate determination of the percent glycated hemoglobin in a single measurement. It is theorized that this competition for binding to the solid phase is affected by the ratio of total hemoglobin to the boronate affinity complex. Preferably, the total hemoglobin/boronate affinity complex ratio is at least about 0.01, and more preferably at least about 0.04. This ratio is believed to be important because excess boronate in the sample mixture disrupts the competition for binding to the solid phase.

Whole blood can be hemolyzed in a variety of ways, either by diluting the whole blood sample in water, or, more preferably, using an agent such as a nonionic surfactant detergent, like TRITON® X-100. Hemolysis releases hemoglobin and its derivatives from the red blood cells for analysis.

The GHb assay according to the present invention is based on the affinity of boronic, phenylboronic, boric acid and boronate etc. (hereinafter "boronate") compounds or moieties for glycated hemoglobin. Boronate reacts with GHb in a sample through the cis-diol moiety of glucose bound to hemoglobin, forming a five-membered ring structure. A boronate group can be attached to a solid phase covalently, by a variety of chemistries, or electrostatically, and methods for doing so have been described in the art, including, for example, U.S. Pat. No. 5,459,080, incorporated herein by reference.

The solid phase itself can be chosen from a variety of materials including, but not limited to beads, microparticles, magnetic microparticles, microtiter plates, tubes, and the like, made of polystyrene, polyacrylamide, agarose, dextran, latex, silica, glass, etc., which may be further derivitized to include functional surface groups. These functional surface groups include, but are not limited to aldehyde, aliphatic amine, aromatic amine, amide, carboxylic acid, sulfhydryl, chloromethyl, epoxy, hydrazide, hydroxyl, etc., which can then be covalently coupled to the boronate or boronate support following standard coupling techniques known to those skilled in the art. Preferred solid phases include amino functionalized magnetic latex particles and particularly preferred carboxylated magnetic latex particles, which have been derivatized to amino particles using a diamine and standard coupling techniques. The diamines include, but are not limited to, ethylenediamine, 1,6-hexanediamine, 1,4-trans-cyclohexanediamine, with ethylenediamine being preferred.

Preferred functional surface moieties for attachment of boronate compounds can be chosen from a variety of materials including, but not limited to, carboxymethylamylose, carboxymethylcellulose, polyaspartic acid, polyglutamic acid, polylysine, polyacrylic acid, proteins, albumins, antibodies, etc. and can be coupled via known techniques to the solid phase. Preferred functional surface moieties are carboxymethylcellulose, with carboxymethylamylose being particularly preferred.

Boronate compounds for use with the method of the invention include those described in Gallop, U.S. Pat. No. 4,496,722, incorporated herein by reference. Preferred compounds include 4-carboxyphenylboronic acid, 3-nitro-5-carboxyphenylboronic acid and m-aminophenylboronic acid (APBA). Particularly preferred is m-aminophenylboronic acid (APBA).

GHb bound to a solid phase through a boronate attachment group may then be detected using an antibody which recognizes a portion of the hemoglobin molecule, such antibody being attached or conjugated to a detectable moiety. The labeled component may be an antibody, and desirably may be a monoclonal or polyclonal antibody (Ab), or Ab fragment containing the antigen binding site, or complementarity determining region (CDR), such as an F(ab')$_2$ or Fab fragment. The detectable moiety or label may be a radioactive, fluorescent or chemiluminescent substance, or an enzyme. Alternatively, a labeled-second Ab which recognizes the species specific Fc fragment of the first Ab may also be used. Also, it is possible to simply have a label as the labeled component. In all cases, signal would be generated and detected depending on the type of labeling substance employed.

As another alternative, in place of an added label, the bound hemoglobin itself, due to its peroxidase-like properties, can generate a detectable signal. This is accomplished by adding hydrogen peroxide, with or without addition of another substrate (e.g. isoluminol).

Preferably, whole blood samples are lysed and diluted using methods known in the art. The blood cells are lysed using agents available to the skilled artisan. Of those, surfactants, and particularly nonionic surfactants, are preferred. A 1:80 dilution is typical, using for example, 0.5% TRITON® X-100 nonionic surfactant. Azo-valeric initiated, carboxylated magnetic microparticles are coated with an amine, preferably ethylenediamine (EDA), to which is attached a polymer, preferably a polymeric anion, and particularly carboxylic acid based polymeric anion, and a boronate compound. Especially preferred is carboxymethylamylose (CMA) and maminophenylboronic acid (APBA) using 1-Ethyl-3-(3-dimethylaminopropyl) carbodiimide hydrochloride (EDAC) as the functional surface moiety. The derivatized microparticle is then incubated with the lysed sample. After washing, monoclonal anti-hemoglobin Ab labeled with acridinium is added. Following incubation and washing, trigger reagents are added and the resulting chemiluminescent signal is measured as Relative Light Units (RLU). Other methods of reading the signal generated by the labeled component are also within the scope of the invention. Calibrators or standards that are run with the assay provide calibration (or standard) curves from which the %GHb in the sample is determined using the measured chemiluminescent signal. The measured chemiluminescent signal is directly proportional to the %GHb in the sample.

EXAMPLES

The following examples serve to demonstrate various embodiments of the invention. These are provided by way of illustration only, and should not be construed as limiting the scope of the invention.

Briefly, %GHb was determined following hemolysis of whole blood to release hemoglobins, after which samples were diluted and incubated with a solid phase having a boronate reactive group to which glycated hemoglobin binds. Subsequently, or simultaneously, the sample mixture was reacted with a labeled anti-hemoglobin Ab. After washing, the resulting signal was detected and was directly proportional to the %GHb in the sample.

The following examples will show different methods for hemolysis and dilution, different means for attaching a boronate group to magnetic microparticles, and use of different anti-hemoglobin antibodies. All methods use a sulfopropyl acridinium ester (10-(3-sulfopropyl)-N-tosyl-N-(2-carboxypropyl)-9-acridinium carboxamide) for chemiluminescent labeling of Ab as set forth and described in U.S. Pat. Nos. 5,468,646 and 5,543,524, incorporated herein by reference, with detection of Relative Light Units (RLU) to quantify the amount of Ab, and therefore %GHb, detected.

Example 1
Boronate Attachment to Magnetic Microparticles

A. CMA/MERQUAT® coated amino microparticles Two ml of amino magnetic microparticles (#AM 40-500, Spherotech, Libertyville, Ill.) at 5% solids were washed 3 times with 10 ml of 50 mM 2-(N-Morpholino) ethanesulfonic acid, pH 6.2 (MES buffer). The washed microparticles were then incubated in 10 ml of MES buffer containing 240 mg of carboxymethylamylose (CMA; #C4947, Sigma, St. Louis, Mo.) and 96 mg of 1-ethyl-3-(3-dimethylaminopropyl) carbodiimide hydrochloride (EDAC) for 60 minutes at room temperature on a rotator. After incubation, the microparticles were washed 3 times with 100 mM taurine buffer, pH 9.0, and resuspended in 10 ml of a 2% Merquat solution.

The CMA/Merquat coated microparticles were used in conjunction with the IMx® GHb Polyanion Reagent (Abbott Laboratories, Abbott Park, Ill.) as will be described below in Example 4.A. and 4.B. This polyanion reagent consists of phenylboronic acid coupled to polyacrylic acid.

B. CMA-APBA coated amino microparticles Two ml of amino magnetic microparticles (#AM 40-500, Spherotech, Libertyville, Ill.) at 5% solids were washed 3 times with 10 ml of MES buffer. The washed microparticles were then incubated in 10 ml of MES buffer containing 240 mg of CMA and 96 mg of EDAC for 60 minutes at room temperature on a rotator. After incubation, the microparticles were attracted to a magnet and the supernatant discarded. Microparticles were washed once with 10 ml of MES buffer, then incubated in 10 ml of MES buffer containing 46.5 mg of maminophenylboronic acid (hemisulfate) (APBA) and 96 mg EDAC for 60 minutes at room temperature on a rotator. After incubation, the microparticles were washed 3 times with 100 mM taurine buffer, pH 9.0, and resuspended in 10 ml of the same buffer.

C. CMC-APBA coated amino microparticles Two ml of amino magnetic microparticles (#AM 40-500, Spherotech, Libertyville, Ill.) at 5% solids were washed 3 times with 10 ml of MES buffer. The washed microparticles were then incubated in 10 ml of MES buffer containing 240 mg of carboxymethylcellulose (CMC) (MW 250,000; #41931-1, Aldrich, Milwaukee, Wis.) and 96 mg of EDAC for 60 minutes at room temperature on a rotator. After incubation, the microparticles were attracted to a magnet and the supernatant discarded. Microparticles were washed once with 10 ml of MES buffer, then incubated in 10 ml of MES buffer containing 46.5 mg of APBA and 96 mg EDAC for 60 minutes at room temperature on a rotator. After incubation, the microparticles were washed 3 times with 100 mM taurine buffer, pH 9.0, and resuspended in 10 ml of the same buffer.

D. PAA-APBA coated amino microparticles Two ml of amino magnetic microparticles (#AM 40-500, Spherotech, Libertyville, Ill.) at 5% solids were washed 3 times with 10 ml of MES buffer. The washed microparticles were then incubated in 10 ml of MES buffer containing 209 mg of 35% polyacrylic acid (PAA) (MW 250,000; #41600-2, Aldrich, Milwaukee, Wis.) a temperature on a rotator. After incubation, the microparticles were attracted to a magnet and the supernatant discarded. Microparticles were washed once with 10 ml of MES buffer, then incubated in 10 ml of MES buffer containing 46.5 mg of APBA and 96 mg EDAC for 60 minutes at room temperature on a rotator. After incubation, the microparticles were washed 3 times with 100 mM taurine buffer, pH 9.0, and resuspended in 10 ml of the same buffer.

E. TREN-CMA-APBA coated carboxyl microparticles Two ml of carboxyl magnetic microparticles (SP1267, Polymer Labs, Shropshire, UK) at 5% solids were washed 3 times with 10 ml of MES buffer. The washed microparticles were then incubated in 10 ml of MES buffer containing 73 mg of Tris (2-aminoethyl)amine (TREN) and 96 mg of EDAC for 60 minutes at room temperature on a rotator. After incubation, the microparticles were attracted to a magnet and the supernatant discarded. Microparticles were washed 3 times with 10 ml of MES buffer, then incubated in 10 ml of MES buffer containing 120 mg CMA mg and 48 mg EDAC for 60 minutes at room temperature on a rotator. After the second incubation, microparticles were washed once with 10 ml of MES buffer, then incubated in 10 ml of MES buffer containing 46.5 mg APBA and 96 mg EDAC for another 60 minutes at room temperature on a rotator. After this final incubation, the microparticles were washed 3 times with 100 mM taurine buffer, pH 9.0, and resuspended in 10 ml of the same buffer.

F. TREN-CMC-APBA coated carboxyl microparticles Two ml of carboxyl magnetic microparticles (SP1267, Polymer Labs, Shropshire, UK) at 5% solids were washed 3 times with 10 ml of MES buffer. The washed microparticles were then incubated in 10 ml of MES buffer containing 73 mg of Tris (2-aminoethyl)amine (TREN) and 96 mg of EDAC for 60 minutes at room temperature on a rotator. After incubation, the microparticles were attracted to a magnet and the supernatant discarded. Microparticles were washed 3 times with 10 ml of MES buffer, then incubated in 10 ml of MES buffer containing 120 mg CMC (MW 700,000; #41933-8, Aldrich, Milwaukee, Wis.) and 48 mg EDAC for 60 minutes at room temperature on a rotator. After the second incubation, microparticles were washed once with 10 ml of MES buffer, then incubated in 10 ml of MES buffer containing 46.5 mg APBA and 96 mg EDAC for another 60 minutes at room temperature on a rotator. After this final incubation, the microparticles were washed 3 times with 100 mM taurine buffer, pH 9.0, and resuspended in 10 ml of the same buffer.

G. APBA coated carboxyl microparticles Two ml of carboxyl magnetic microparticles (SP1340, Polymer Labs, Shropshire, UK) at 5% solids were washed 3 times with 10 ml of MES buffer. The washed microparticles were then incubated in 10 ml of MES buffer containing 43.2 mg of APBA and 96 mg of EDAC for 60 minutes at room temperature on a rotator. After incubation, the microparticles were washed twice with 10 ml of 50 mM taurine buffer, pH 9.0, and resuspended in 10 ml of the same buffer.

H. EDA-CMA-APBA coated carboxyl microparticles Two ml of azo-valeric initiated carboxylated magnetic microparticles (AB007C, Polymer Labs, Shropshire, UK) at 5% solids were washed 3 times with 10 ml of MES buffer. The washed microparticles were then incubated in 10 ml of MES buffer containing 15 l of ethylenediamine (EDA) and 10 mg of EDAC for 60 minutes at room temperature on a rotator. After incubation, the microparticles were attracted to a magnet and the supernatant discarded. Microparticles were washed 3 times with 10 ml of MES buffer, then incubated in 10 ml of MES buffer containing 120 mg CMA mg and 19.6 mg EDAC for 60 minutes at room temperature on a rotator. After the second incubation, microparticles were washed once with 10 ml of MES buffer, then incubated in 10 ml of MES buffer containing 46.5 mg APBA and 96 mg EDAC for another 60 minutes at room temperature on a rotator. After this final incubation, the microparticles were washed 3 times with 50 mM taurine buffer, pH 9.0, and resuspended in 10 ml of the same buffer.

Example 2

Antibody Conjugation with Acridinium

Antibody to be conjugated was first dialyzed against 3 changes of phosphate buffered saline (PBS), utilizing 4 to 6 hours per dialysis change. Antibody was then diluted to a concentration of 1 mg/ml. While mixing the 1 mg/ml antibody solution, 10% 3-[(3-cholamidopropyl) dimethyammonio]-1-propane sulfonate (CHAPS) and 5 ug/ml sulfopropyl acridinium ester was added. This was mixed for 10 minutes at room temperature then loaded onto a120 ml bed volume (1.6×60 cm) Pharmacia Sephacryl S-200 column. The column buffer used was 2.28 mM sodium phosphate monobasic, 7.68 mM sodium phosphate dibasic, 145 mM NaCl, 0.1% CHAPS, pH 6.3. One ml fractions were collected, and those fractions with an absorbance at 280 nm greater than or equal to 0.1 were pooled. The acridinium-labeled antibody was diluted to a final concentration of 40 ng/ml in Conjugate Diluent (10 mM MES, 150 mM NaCl, pH 6.3 containing 2% bovine serum albumen (BSA) and 0.5% TRITON® X-100).

Example 3

GHb Assay Protocol

Microparticles were washed with 100 mM taurine buffer, pH 9.0 and resuspended in the same buffer at 0.1% solids, unless stated otherwise. Whole blood samples were lysed and diluted, then 50 l of sample was mixed with 50 l of microparticles and incubated at 37° C. for 18 minutes. The particles were then attracted to a magnet and washed 4 times with 1 ml of Common Buffer (4 mM sodium phosphate, 150 mM NaCl, pH 7.5 containing 0.05% Brij and 0.1% $NaN_3$).

Fifty microliters of acridinium-labeled antibody to human hemoglobin, prepared as in Example 2., was added to the washed microparticles. Labeled antibody was incubated with microparticles for 4 minutes at 37° C., then particles were attracted to a magnet and washed 4 times with 1 ml of Common Buffer.

Chemiluminescent signal was generated by adding Trigger Reagents of 0.053% $HNO_3$, 1.2% $H_2O_2$ and 0.9% Diethylenetriaminepentaacetic acid (DPTA) followed by 0.35 N NaOH and 2% TRITON® X-100. The chemiluminescent signal was measured in Relative Light Units (RLU).

Example 4

Use of Boronate Magnetic Microparticles in GHb Assay

Six to eight whole blood samples were selected for testing that would cover a clinical range of %GHb levels based on their %GHb levels in the lMx® GHb assay(Abbott Laboratories, Abbott Park, Ill.).

A. CMA/Merguat coated particles: Sample+Polyanion Reagent Whole blood samples were lysed by diluting them 1:5 in distilled water. The hemolysate was then further diluted 1:16 in 0.5% TETRONIC® 1307 (BASF #550193, Mount Olive, N.J.) in PBS. Microparticles prepared in Example 1.A. were washed with 100 mM taurine buffer, pH 9.0, then resuspended in the same taurine buffer at 0.1% solids. The diluted whole blood samples were mixed with an equal volume of the lMx® GHb Polyanion Reagent (Abbott Laboratories, Abbott Park, Ill.) and incubated at 37° C. for 7 minutes to allow the GHb in the sample to bind to the boronate group of the Polyanion Reagent. After incubation, 50 l of this mixture was mixed with 50 l of microparticles, incubated and washed as in Example 3.

A DEAE-purified mouse monoclonal antibody ($IgG_1$)to human hemoglobin (clone MIH 9505, Medix Biotech, Inc., San Carlos, Calif.) which had been labeled with acridinium as in Example 2., was added to the washed microparticles and the experiment completed as in Example 3. FIG. 1 shows that the chemiluminescent signal (RLU) was directly proportional (R=0.956) to the %GHb in the sample.

B. CMA/Merguat coated particles+Polyanion Reagent The CMA/Merguat coated microparticles from Example 1.A. were overcoated with the lMx® GHb Polyanion Reagent (Abbott Laboratories, Abbott Park, Ill.) by washing the microparticles with 100 mM taurine buffer, pH 9.0 and resuspending them in the Polyanion Reagent at 0.1% solids. Microparticles were then washed with 100 mM taurine buffer, pH 9.0 to remove excess Polyanion Reagent, and resuspended in the taurine buffer at 0.1% solids.

Figure 2:
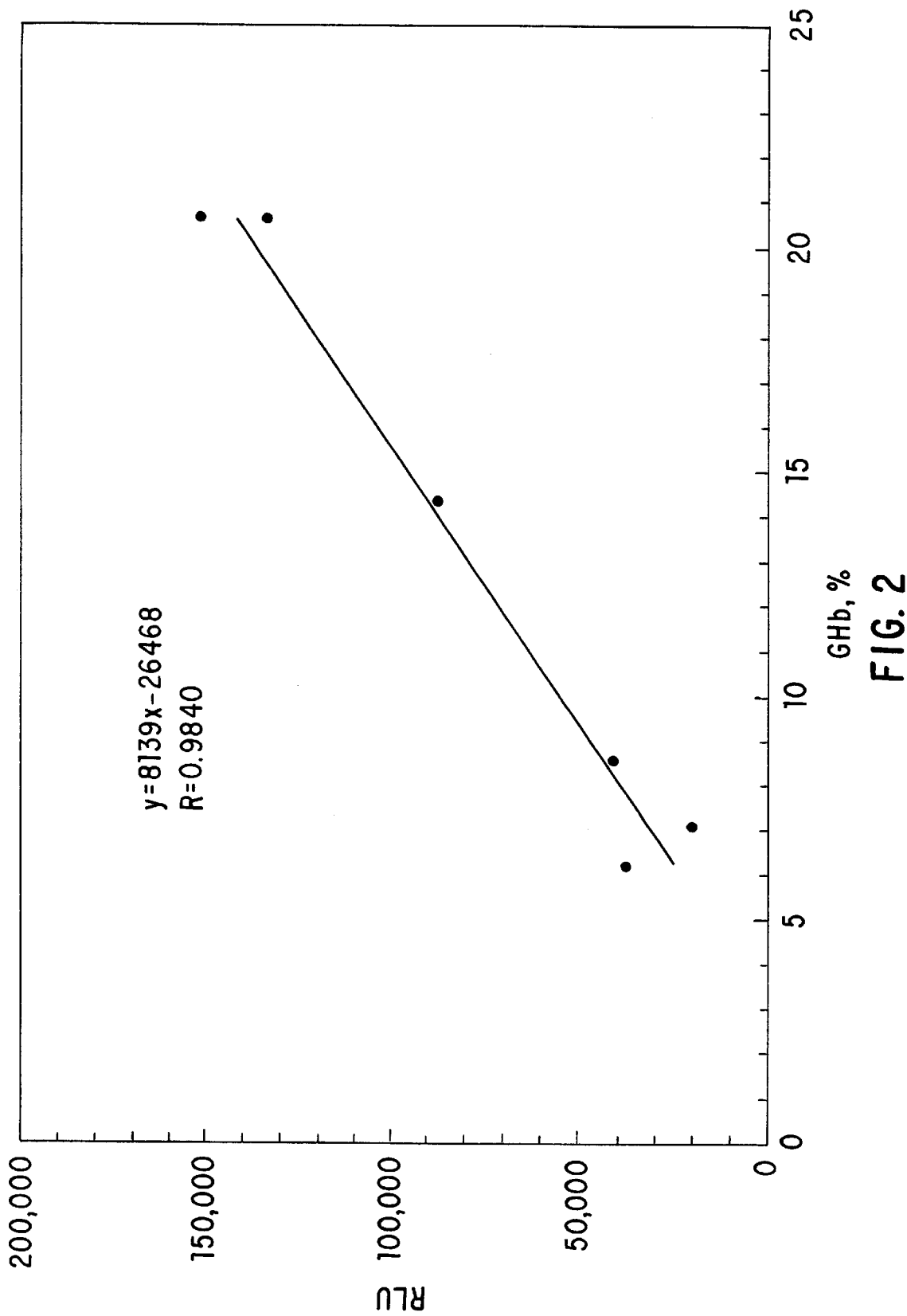
FIG. 2 is a graph illustrating the results of testing whole blood samples to determine %GHb levels using CMA/Merquat coated particles with polyanion reagent according to one embodiment of the invention.

Fifty microliters of sample hemolysate, prepared as in Example 4.A., was then mixed with 50 l of microparticles and the GHb assay was performed as described in Example 3 using the same antibody as in Example 4.A. FIG. 2 shows that the chemiluminescent signal (RLU) was directly proportional (R=0.984) to the %GHb in the sample.

Figure 3:
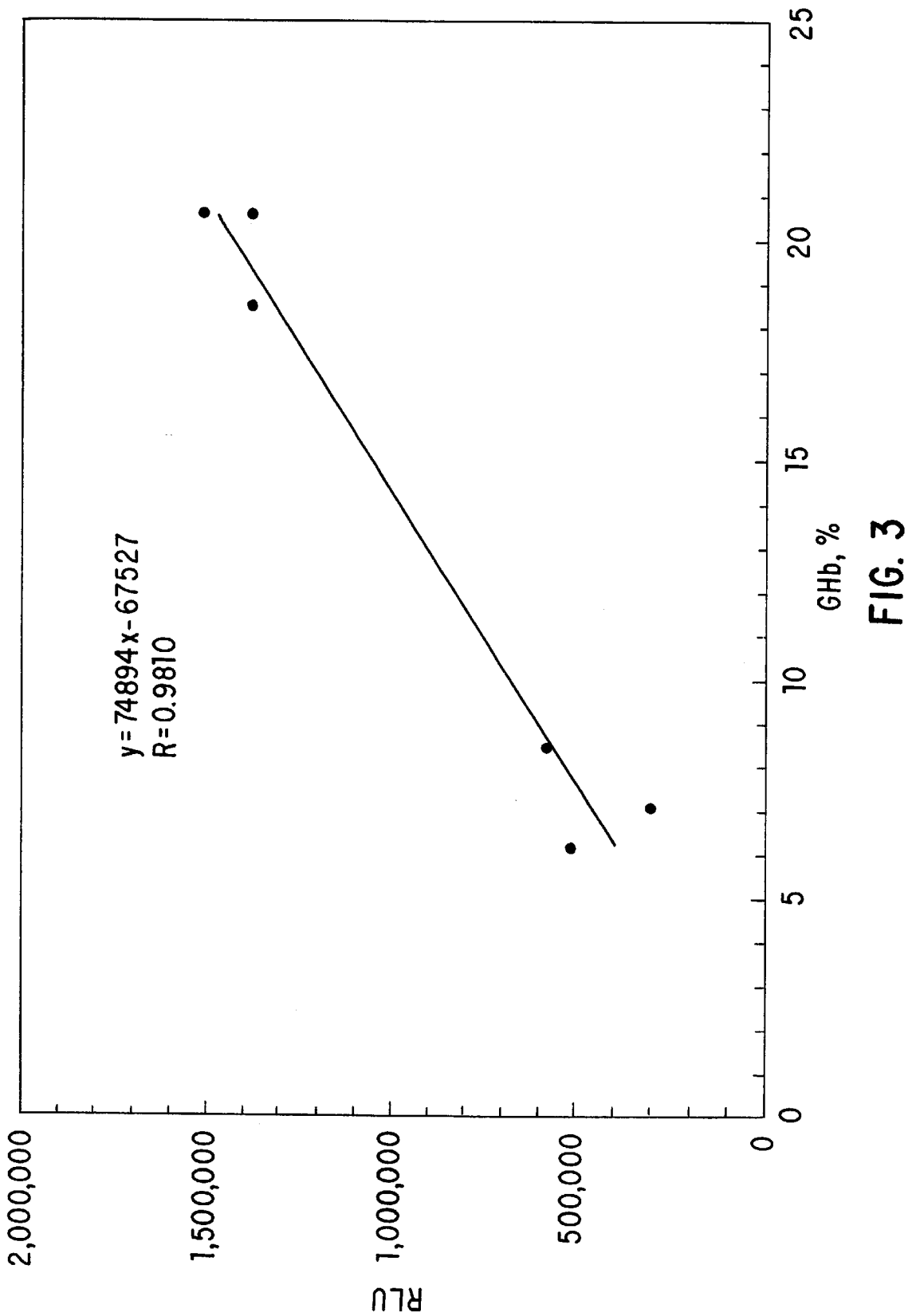
FIG. 3 is a graph illustrating the results of testing whole blood samples to determine %GHb levels using CMA-APBA coated particles according to one embodiment of the invention.

C. CMA-APBA coated particles Whole blood samples were selected as in Example 4.A. and hemolyzed by diluting 1:80 in 0.5% TRITON® X-100 in distilled water. The GHb assay was then performed as in Example 3. using the microparticles from Example 1.B. and the same antibody as in Example 4.A. FIG. 3 shows that the chemiluminescent signal (RLU) was directly proportional (R=0.981) to the %GHb in the sample.

Figure 4:
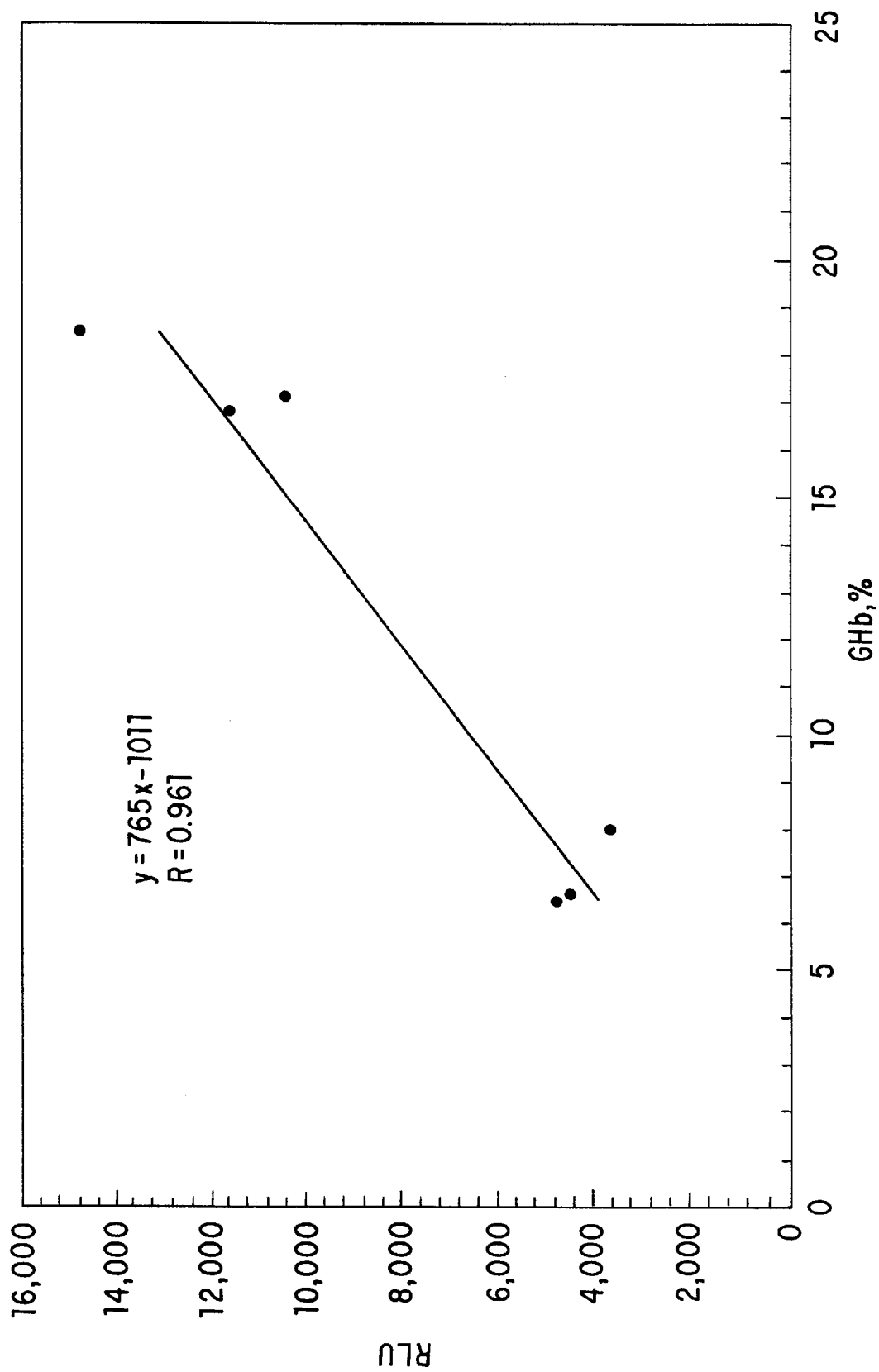
FIG. 4 is a graph illustrating the results of testing whole blood samples to determine %GHb levels using CMC-APBA coated particles according to one embodiment of the invention.

D. CMC-APBA coated particles The GHb assay was performed as in Example 3. using samples prepared as in Example 4.C., the microparticles from Example 1.C. and the same antibody as in Example 4.A. FIG. 4 shows that the chemiluminescent signal (RLU) was directly proportional (R=0.961) to the %GHb in the sample.

Figure 5:
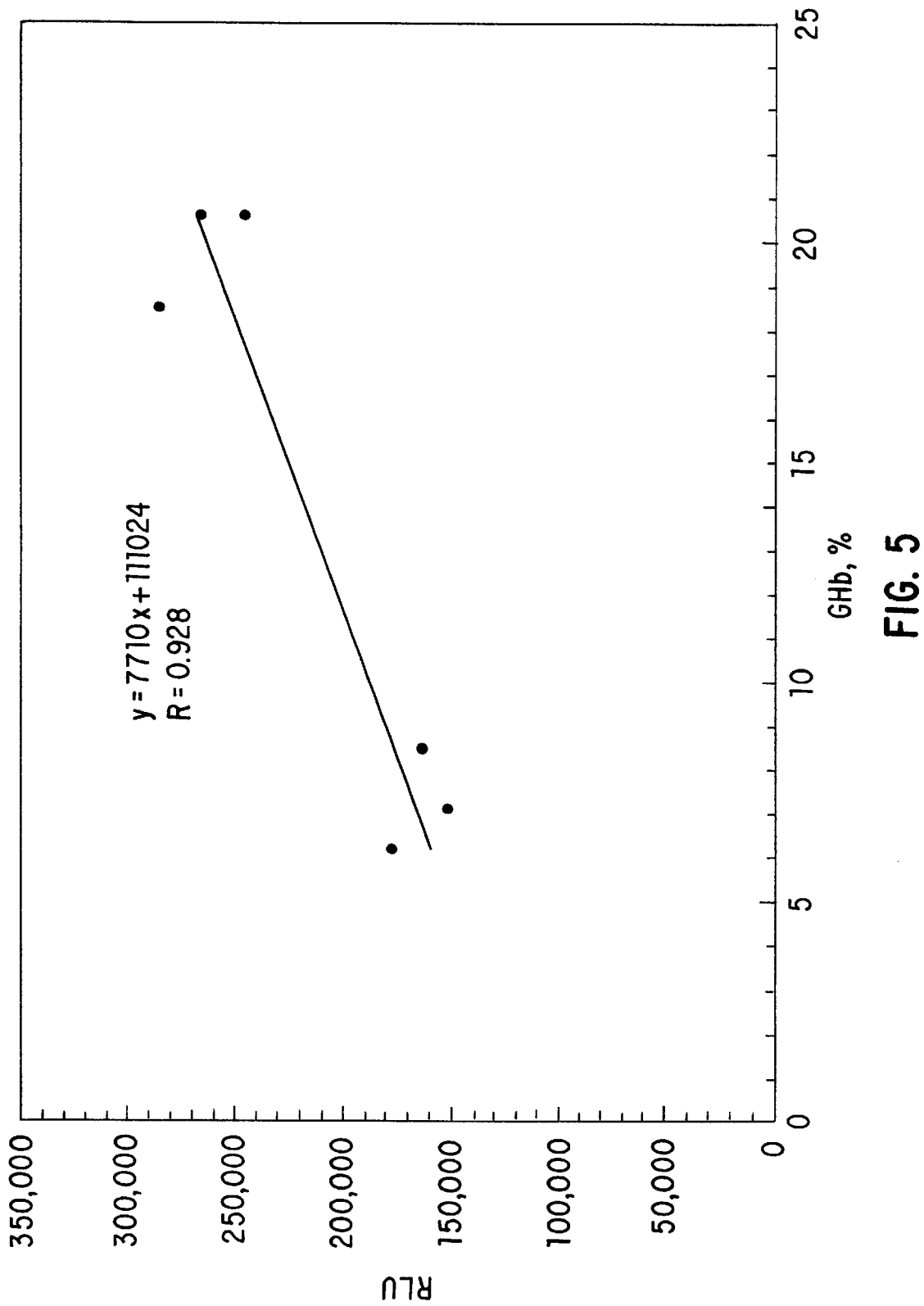
FIG. 5 is a graph illustrating the results of testing whole blood samples to determine %GHb levels using PAA-APBA coated particles according to one embodiment of the invention.

E. PAA-APBA coated particles The GHb assay was performed as in Example 3. using samples prepared as in Example 4.C., the microparticles from Example 1.D. and the same antibody as in Example 4.A. FIG. 5 shows that the chemiluminescent signal (RLU) was directly proportional (R=0.928) to the %GHb in the sample.

Figure 6:
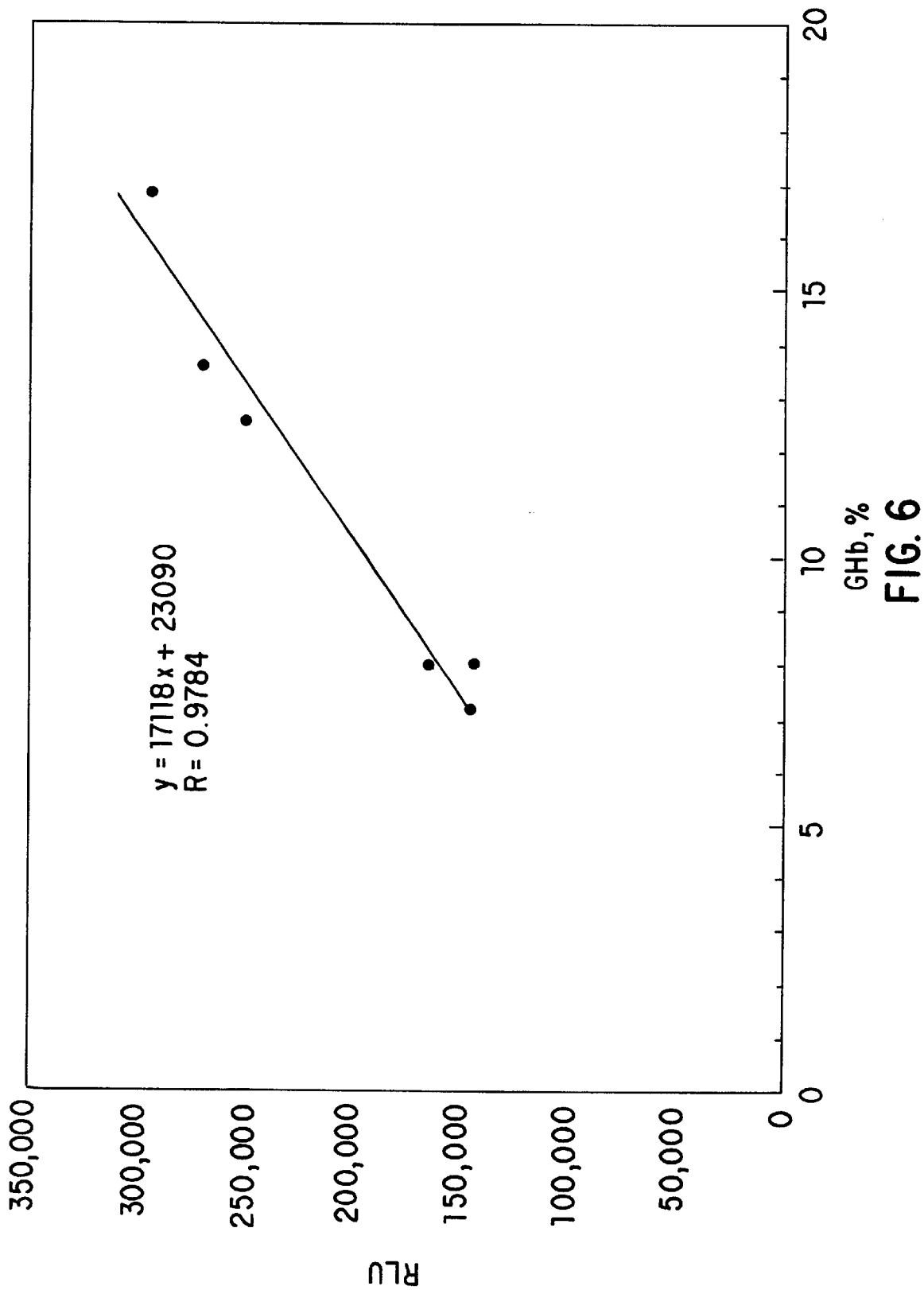
FIG. 6 is a graph illustrating the results of testing whole blood samples to determine %GHb levels using TREN-CMA-APBA coated particles according to one embodiment of the invention.

F. TREN-CMA-APBA coated particles The GHb assay was performed as in Example 3. using samples prepared as in Example 4.C., the microparticles from Example 1.E. and the same antibody as in Example 4.A. FIG. 6 shows that the chemiluminescent signal (RLU) was directly proportional (R=0.978) to the %GHb in the sample.

Figure 7:
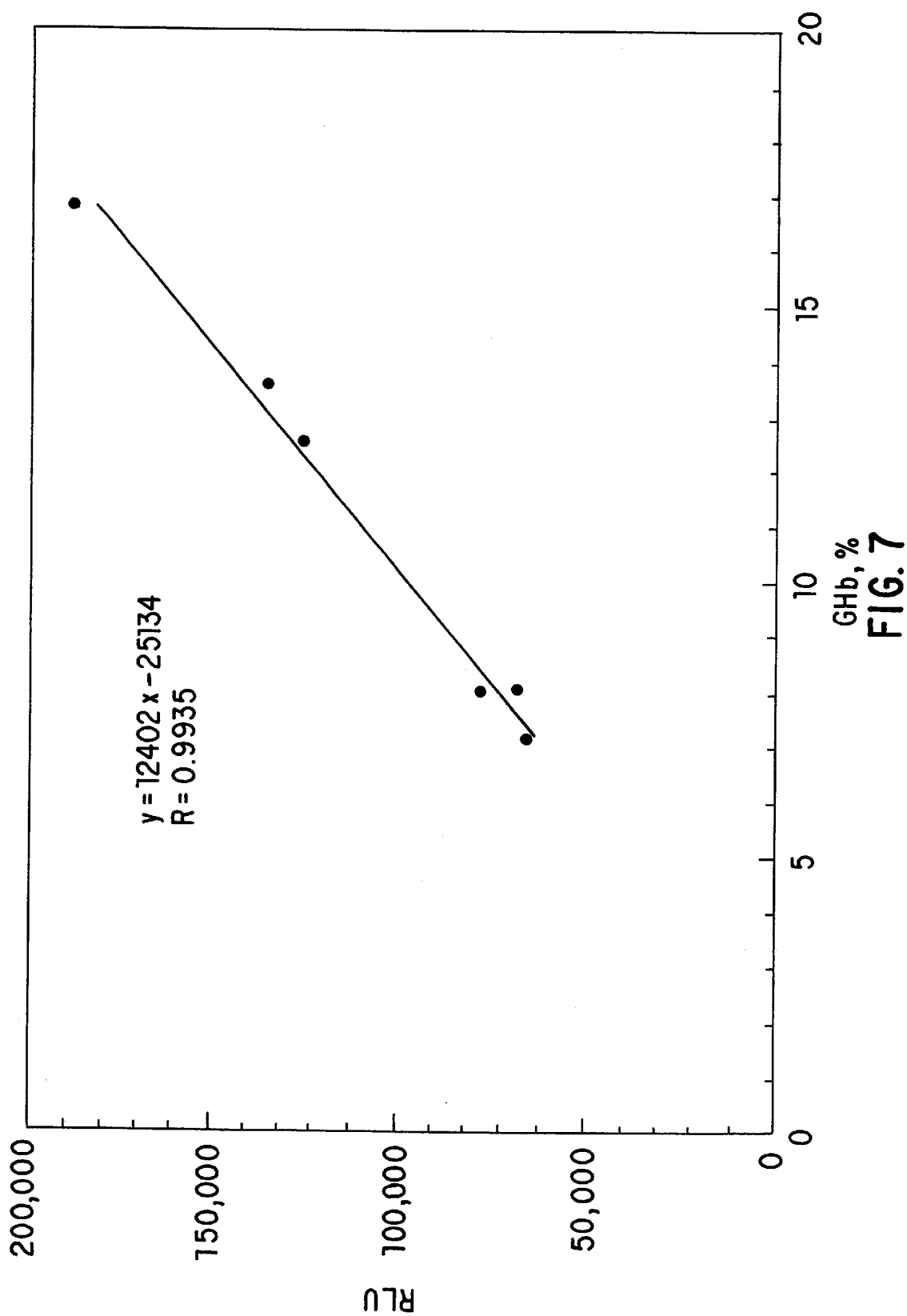
FIG. 7 is a graph illustrating the results of testing whole blood samples to determine %GHb levels using TREN-CMC-APBA coated particles according to one embodiment of the invention.

G. TREN-CMC-APBA coated particles The GHb assay was performed as in Example 3. using samples prepared as in Example 4.C., the microparticles from Example 1.F. and the same antibody as in Example 4.A. FIG. 7 shows that the chemiluminescent signal (RLU) was directly proportional (R=0.994) to the %GHb in the sample.

Figure 8:
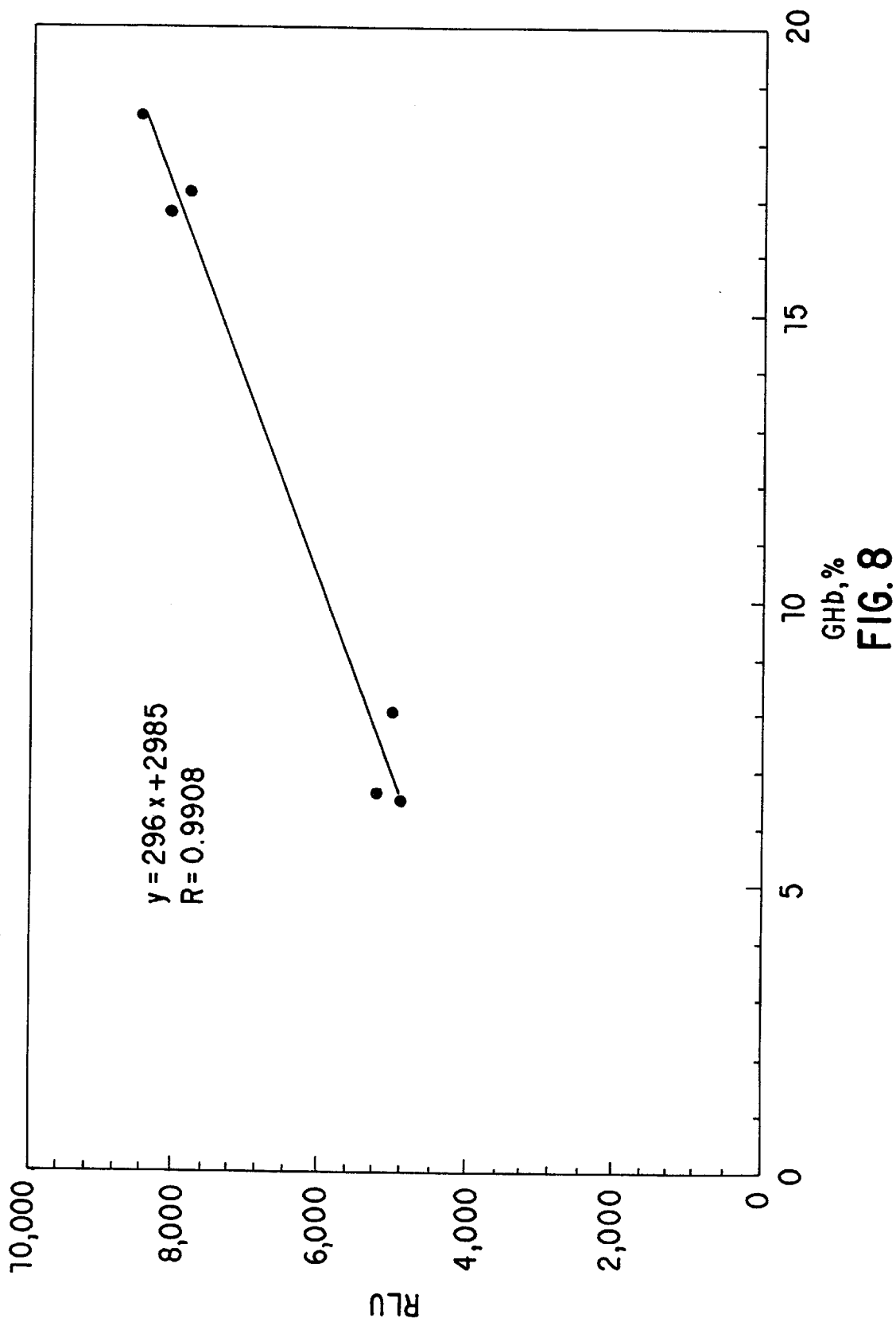
FIG. 8 is a graph illustrating the results of testing whole blood samples to determine %GHb levels using APBA coated particles according to one embodiment of the invention.

H. APBA coated particles The GHb assay was performed as in Example 3. using samples prepared as in Example 4.C., the microparticles from Example 1.G. and the same antibody as in Example 4.A. FIG. 8 shows that the chemiluminescent signal (RLU) was directly proportional (R=0.991) to the %GHb in the sample.

Figure 8A:
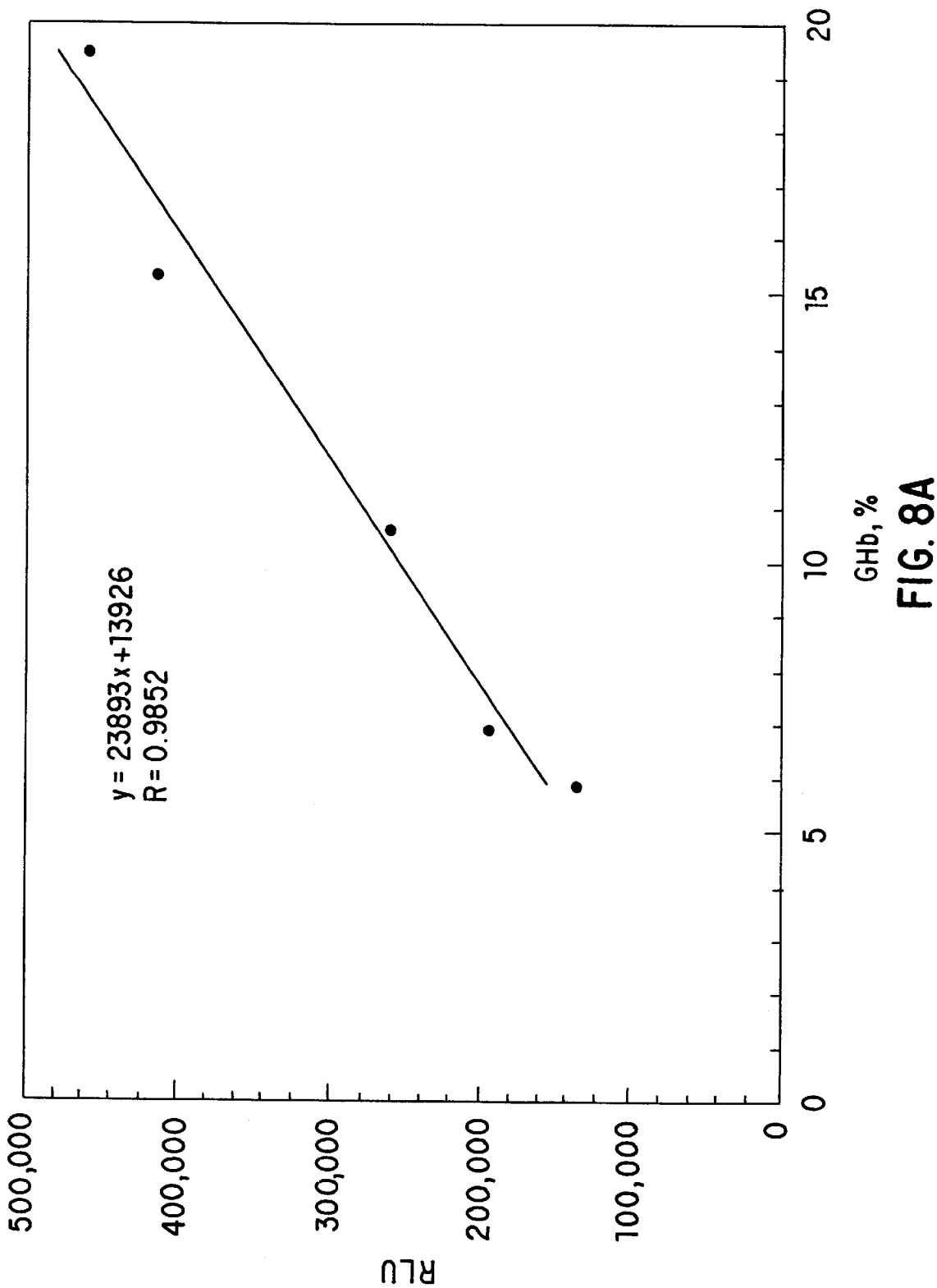
FIG. 8A is a graph illustrating the results of testing whole blood samples to determine %GHb levels using EDA-CMA-APBA coated particles according to one embodiment of the invention.

I. EDA-CMA-APBA coated particles The GHb assay was performed as in Example 3. using samples prepared as in Example 4.C., the microparticles from Example 1.H. and the same antibody as in Example 4.A. (The procedure in this format is referred to as the IPLS GHb assay.) FIG. 8A shows that the chemiluminescent signal (RLU) was directly proportional (R=0.985) to the %GHb in the sample.

Example 5

Correlation of IPLS GHb Assay with Biorad Diamat HPLC and Abbott lMx® GHb 110 whole blood samples were obtained from a hospital lab, where previously they had been tested for GHb using the Biorad Diamat HPLC method to obtain %HbA1c levels. Boronate affinity binding methods, such as are used in the assays described here, detect all GHb species, including HbA1c. Since there is a linear relationship between GHb and HbA1c, comparisons can be made between tests measuring GHb and HbA1c.

Figure 9:
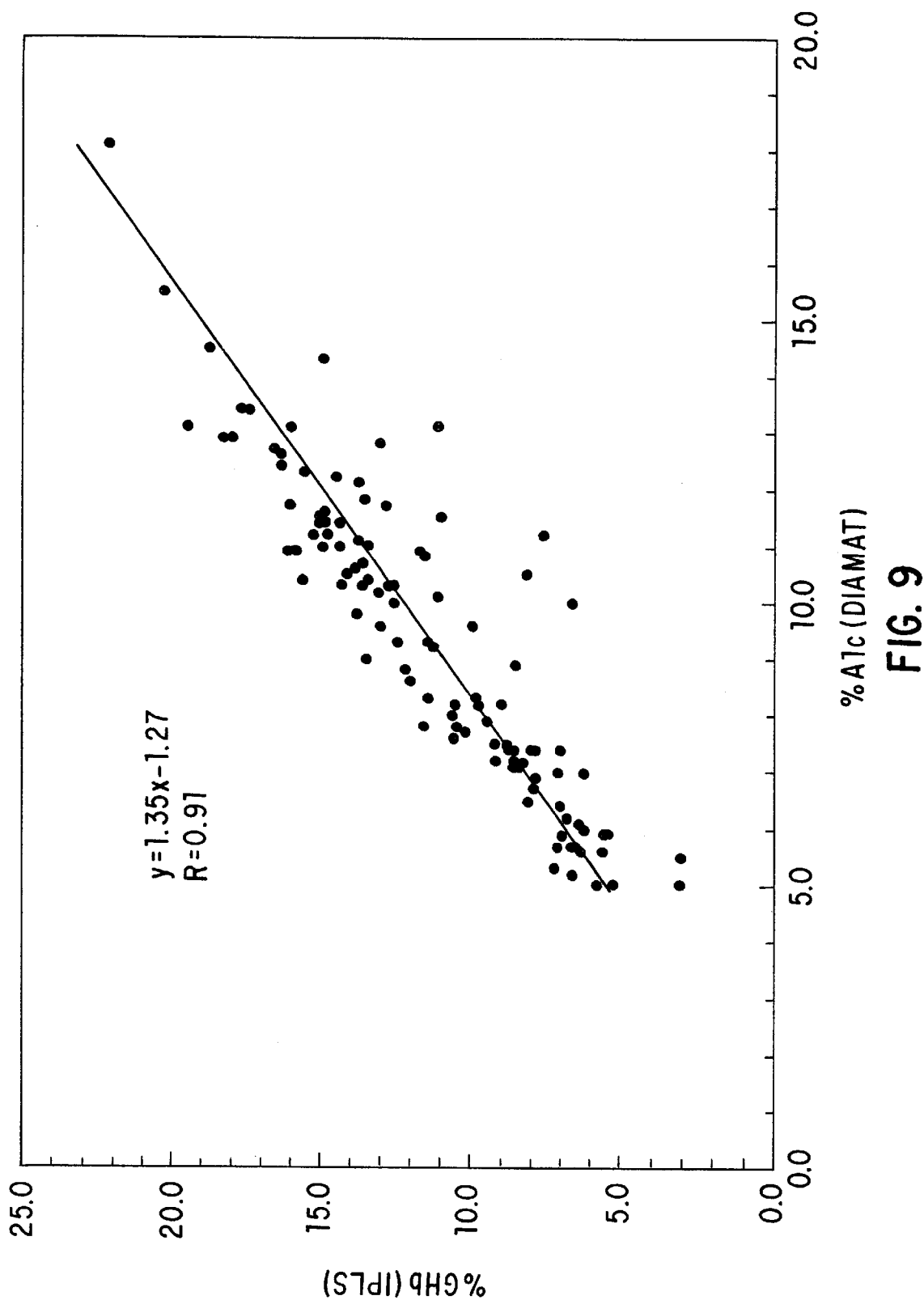
FIG. 9 is a graph illustrating the correlation between %GHb levels determined using the Biorad Diamat HPLC and the preferred embodiment of the invention.
Figure 10:
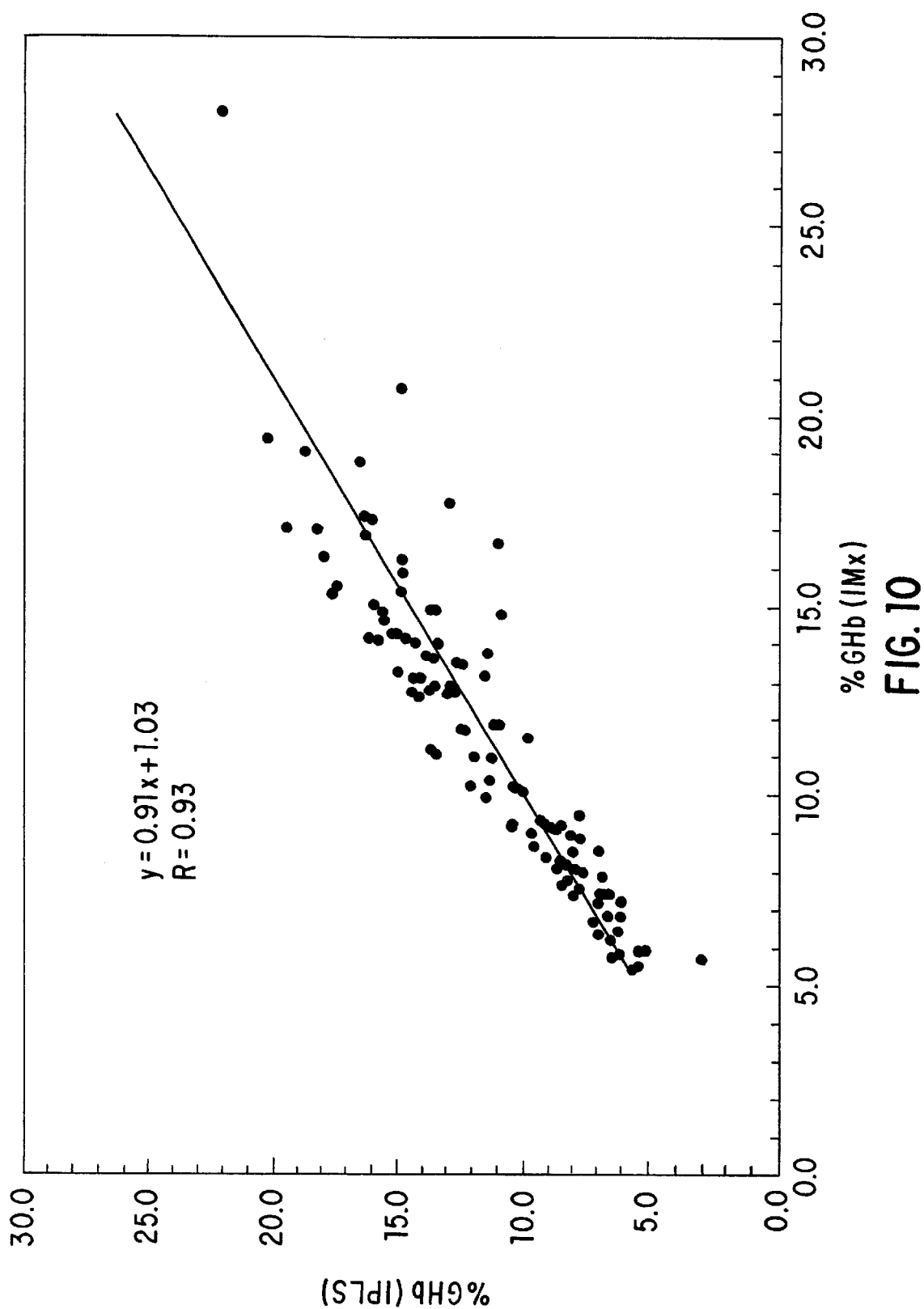
FIG. 10 is a graph illustrating the correlation between %GHb levels determined using the Abbott IMx® GHb assay and the preferred embodiment of the invention.

The IPLS GHb assay was performed as in Example 4.1. with the 110 samples prepared as in Example 4 .C. Results were correlated with the Biorad Diamat HPLC (Brea, Calif.) and IMx® GHb (Abbott Laboratories, Abbott Park, Ill.) assays (FIGS. 9 and 10 respectively).

The correlation between the IPLS GHb and the Biorad Diamat HPLC assays (FIG. 9) was 91%. The correlation between the IPLS GHb and the IMx® GHb assays (FIG. 10) was 93%.

Figure 11:
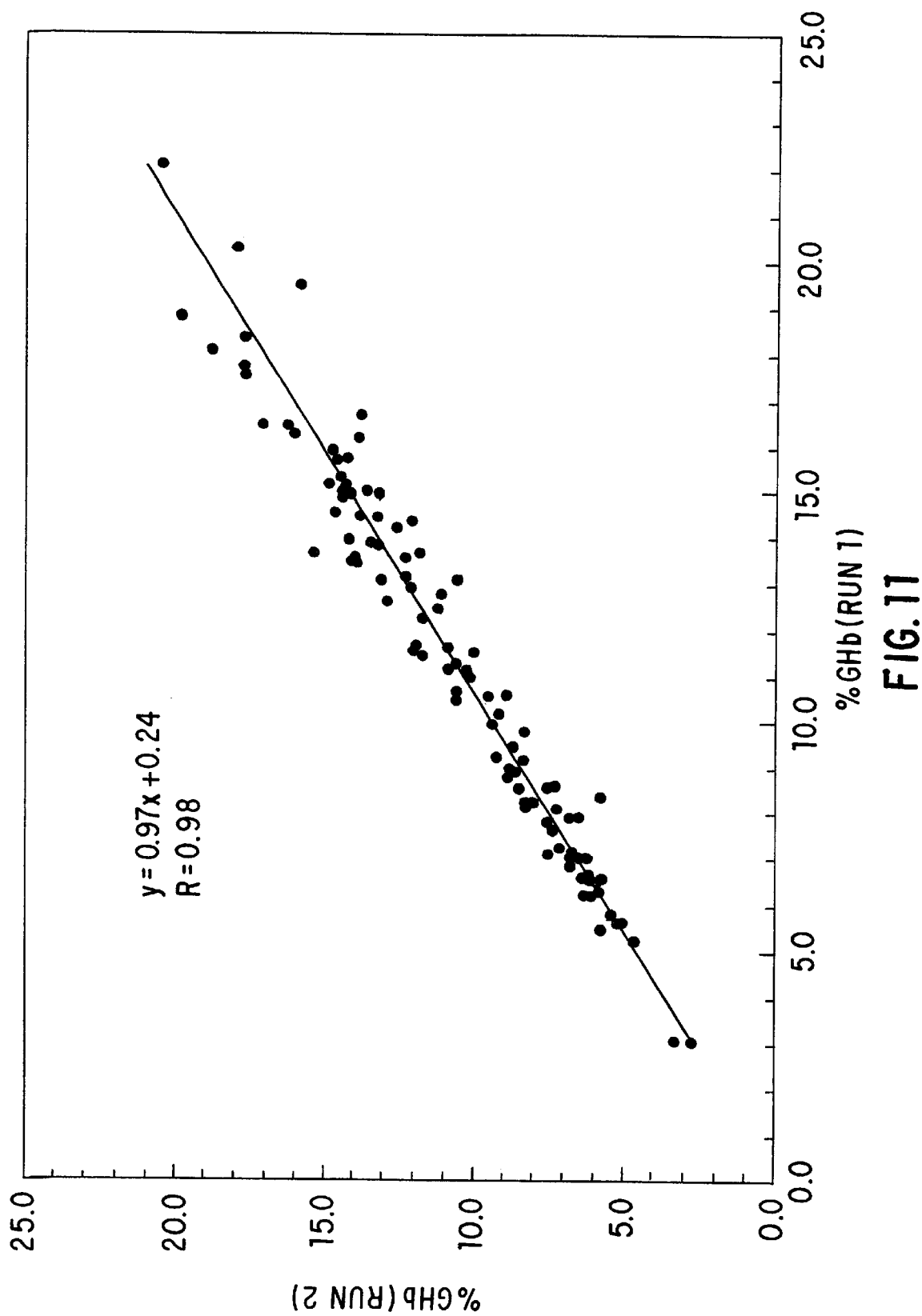
FIG. 11 is a graph illustrating a run-to-run correlation when determining %GHb levels using the preferred embodiment of the invention.

Additionally, two runs were performed on the same 110 samples using the IPLS GHb assay to determine the run-to-run correlation. The results, shown in FIG. 11., indicated excellent agreement (98%) between the two runs (Run 1 vs. Run 2).

Example 6

One Step Format

Figure 12:
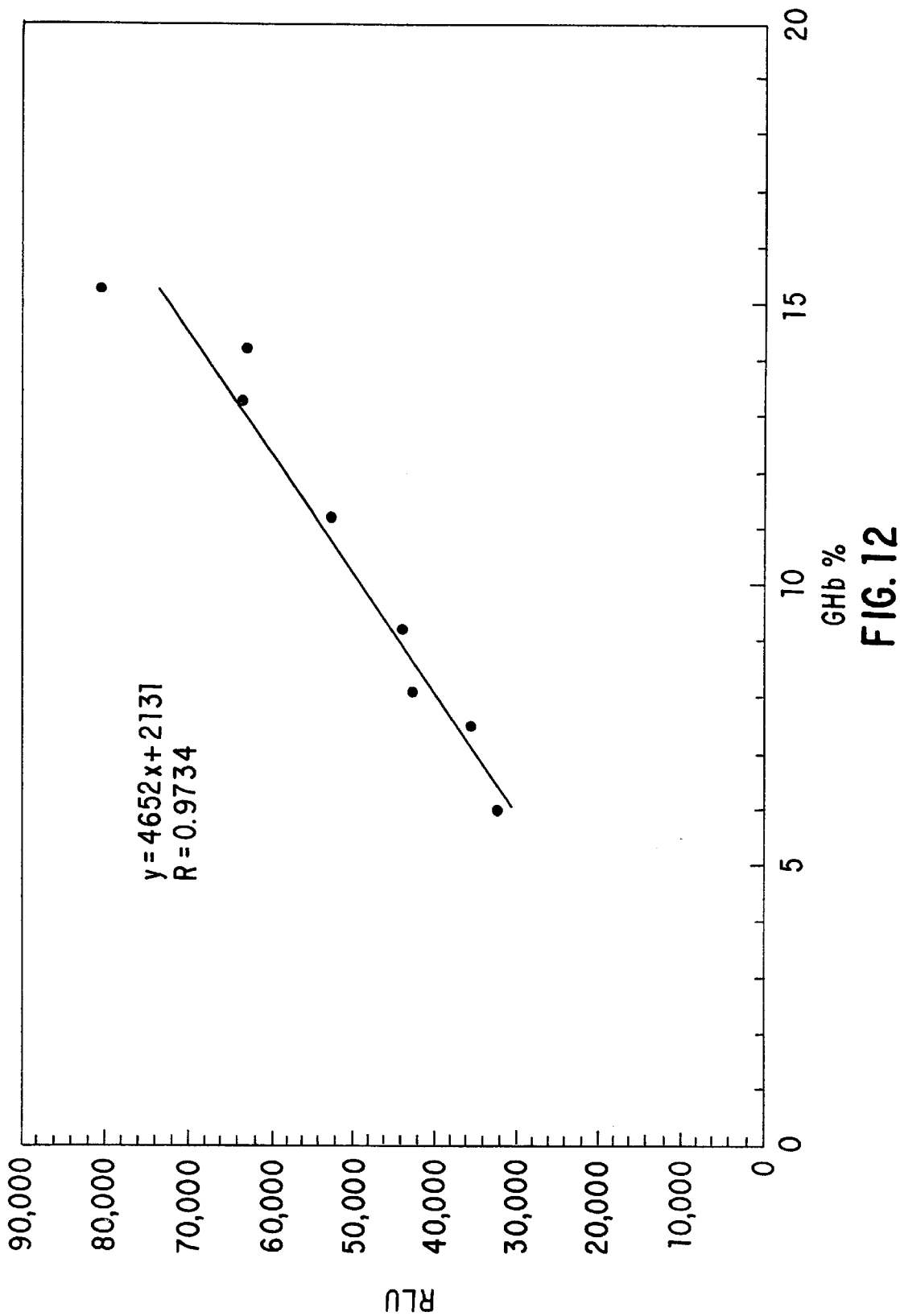
FIG. 12 is a graph illustrating the results of testing whole blood samples to determine %GHb levels using a one-step (simultaneous) format according to one embodiment of the invention.
Figure 13:
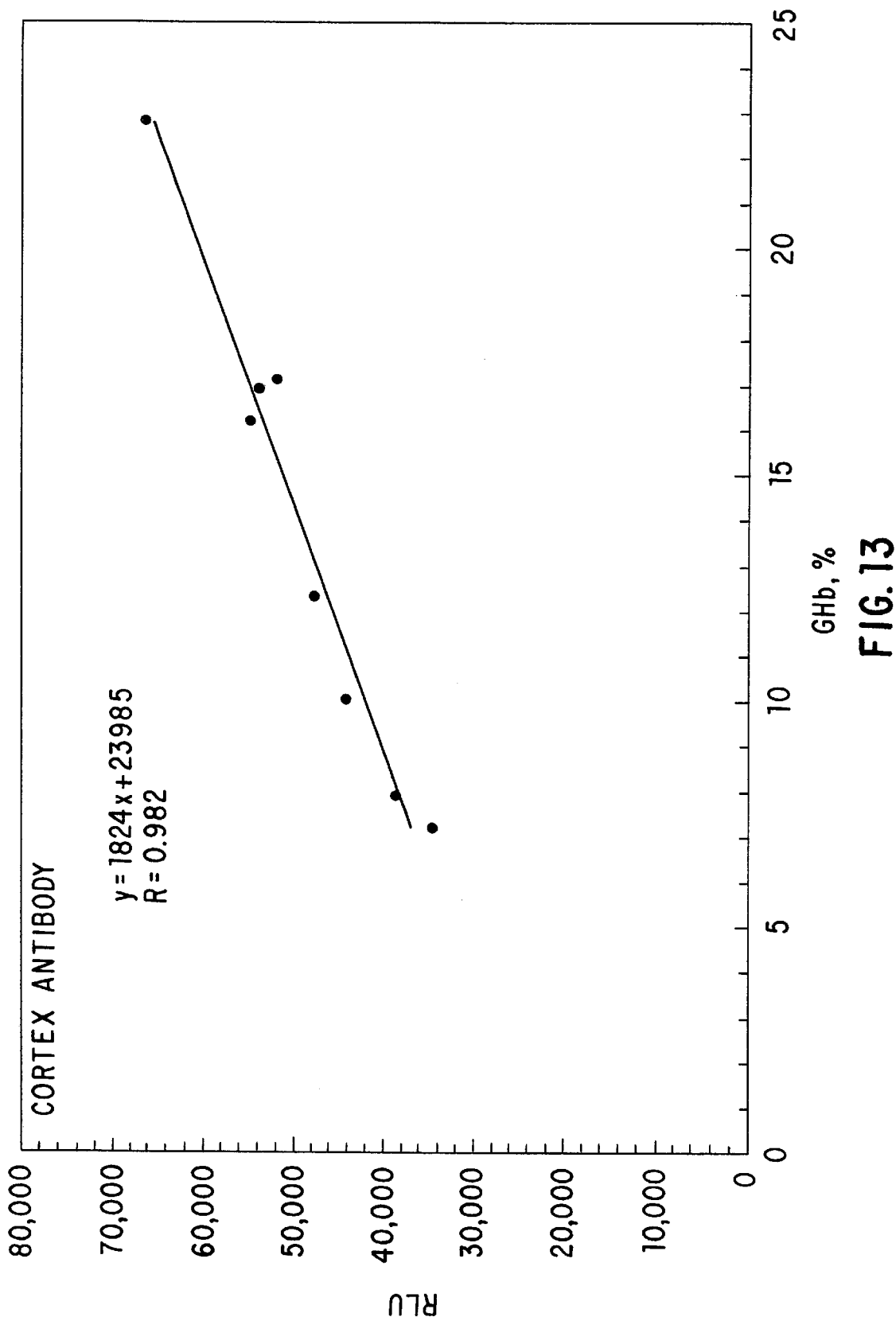
FIG. 13 is a graph illustrating the results of testing whole blood samples to determine %GHb levels using Cortex polyclonal goat anti-human hemoglobin labeled with acridinium according to one embodiment of the invention.
Figure 14:
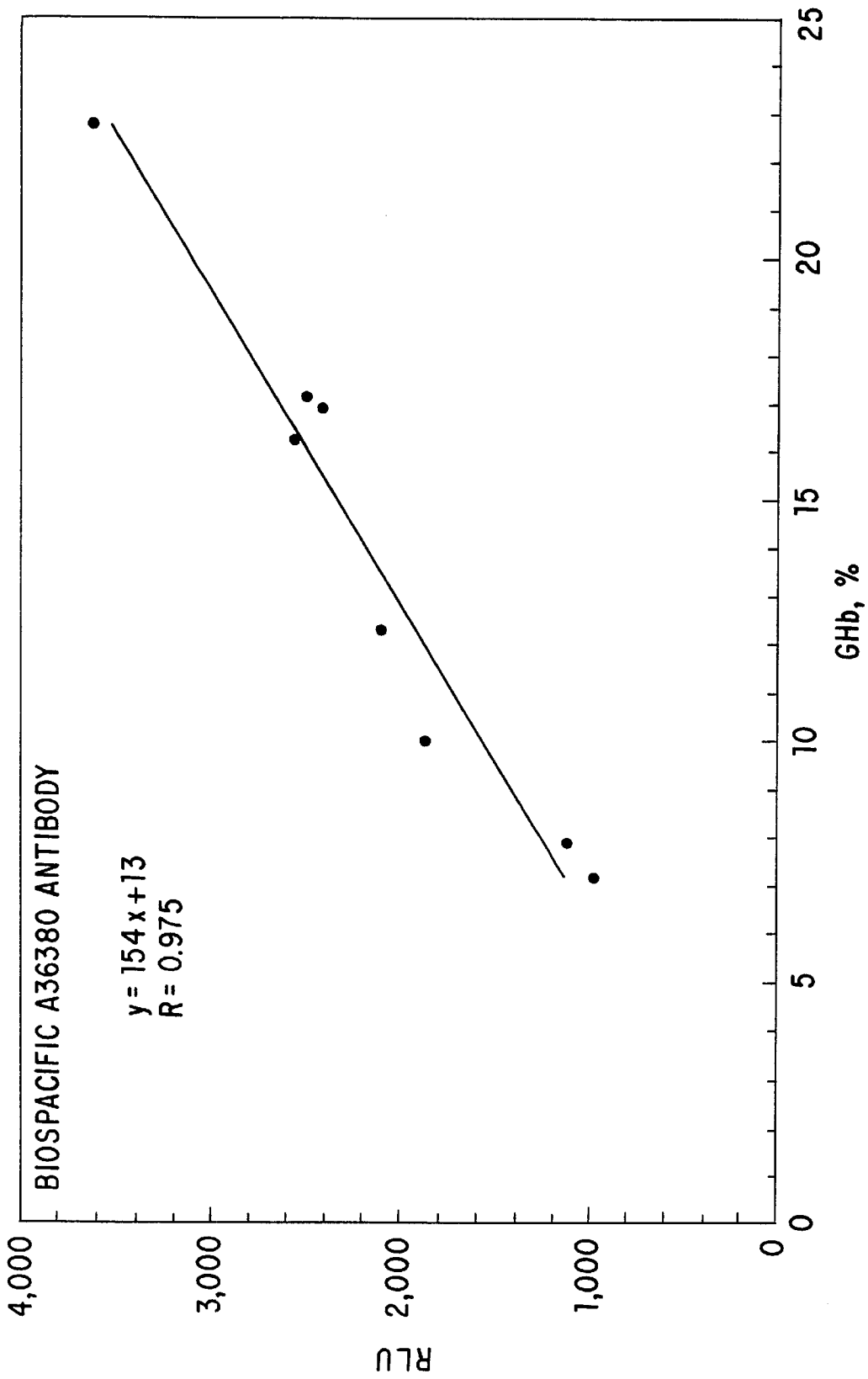
FIG. 14 is a graph illustrating the results of testing whole blood samples to determine %GHb levels using BiosPacific monoclonal anti-human hemoglobin labeled with acridinium according to one embodiment of the invention.
Figure 15:
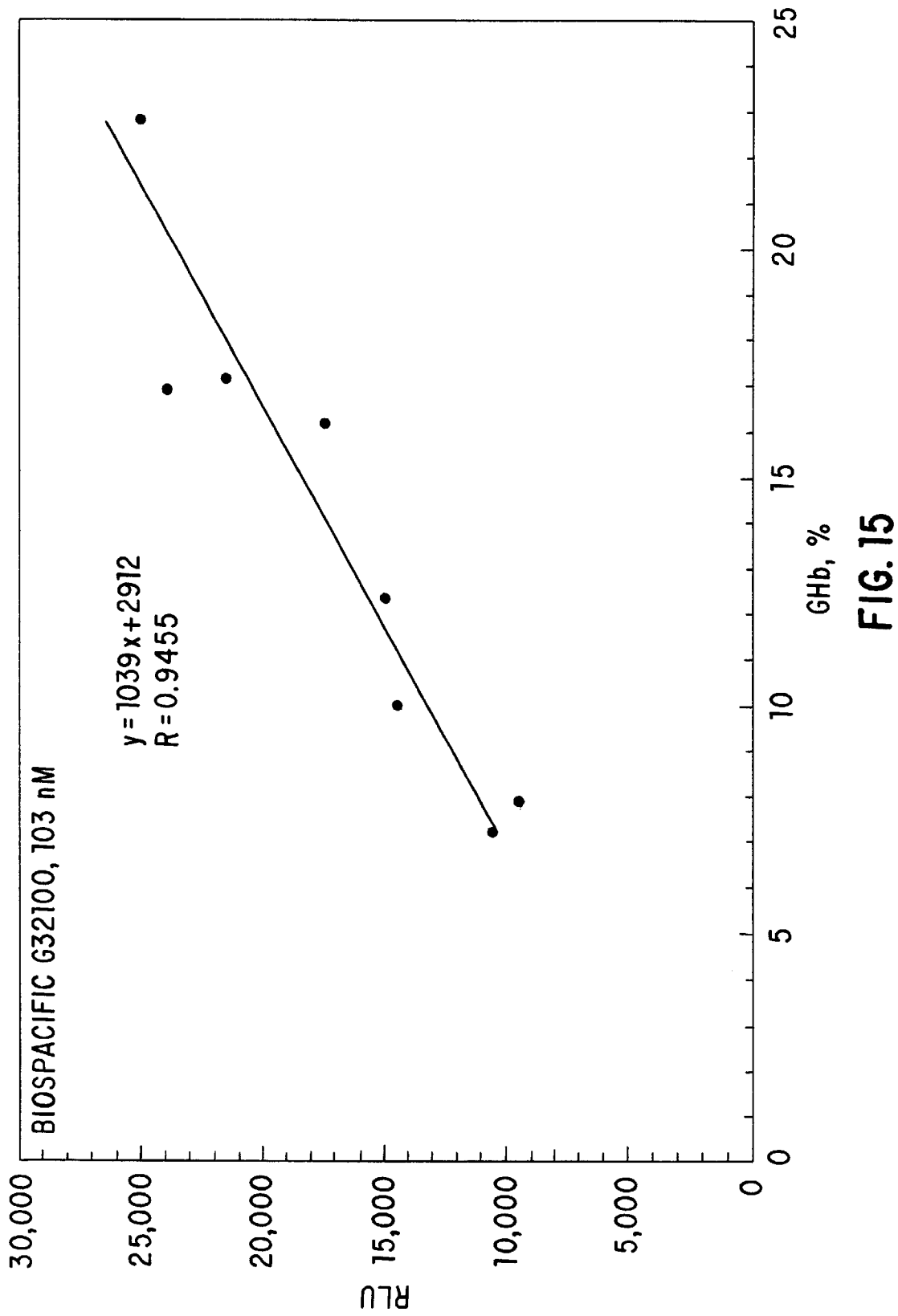
FIG. 15 is a graph illustrating the results of testing whole blood samples to determine %GHb levels using BiosPacific polyclonal goat anti-human hemoglobin labeled with acridinium according to one embodiment of the invention.
Figure 16:
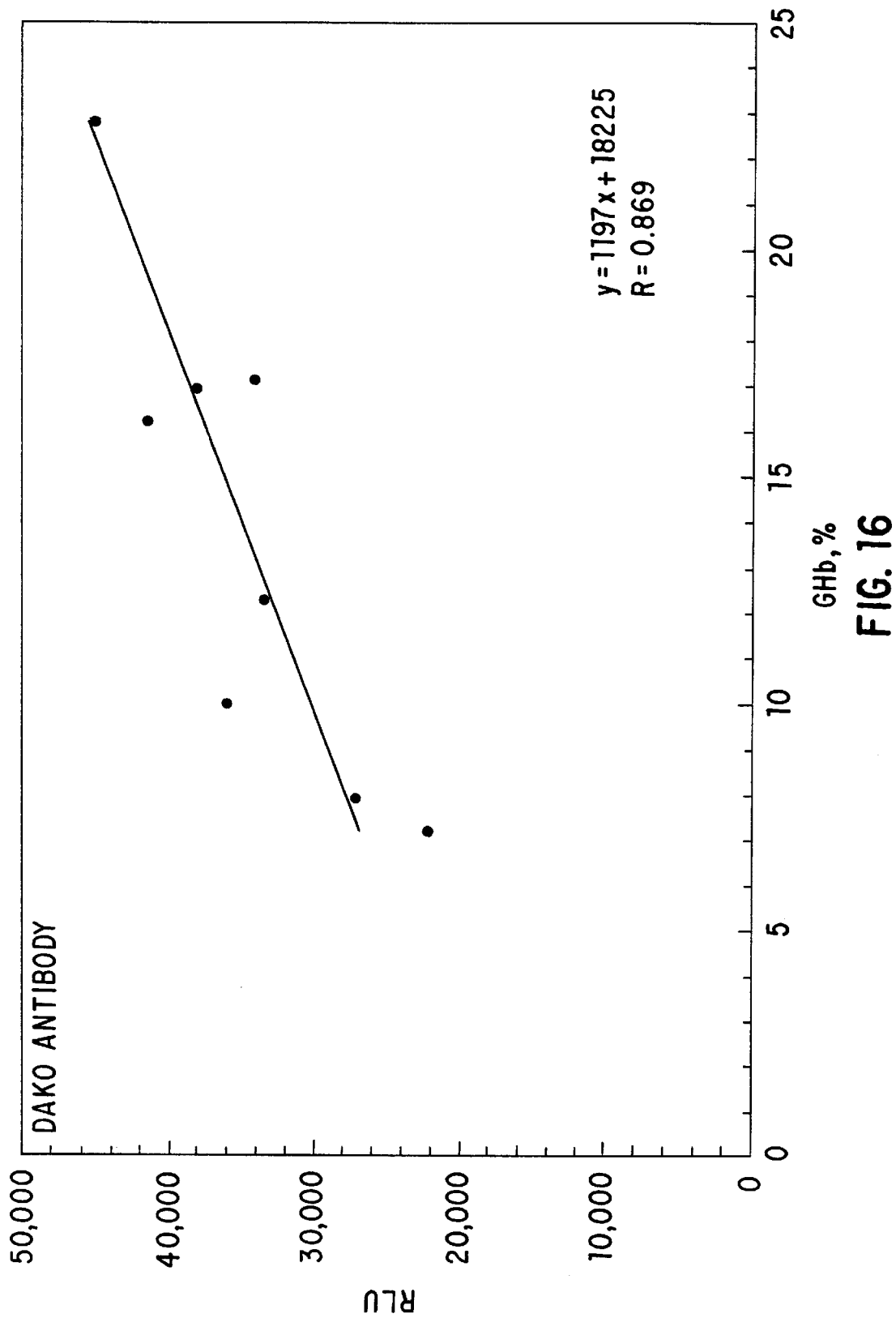
FIG. 16 is a graph illustrating the results of testing whole blood samples to determine %GHb levels using Dako polyclonal rabbit anti-human hemoglobin labeled with acridinium according to one embodiment of the invention.

The hemolysate samples were prepared as in Example 4.C. Microparticles, prepared in Example 1.H., were washed with 50 mM taurine buffer, pH 9.0 and resuspended in the same buffer at 0.1% solids. The labeled antibody was the same antibody as in Example 4.A. The assay was performed by incubating 50 l of hemolysate, 50 l of microparticles and 50 l of acridinium-labeled antibody at 37° C. for 25 minutes. The particles were then attracted to a magnet and washed 4 times with 1 ml of Common Buffer. Chemiluminescent signal was generated by adding Trigger Reagents. FIG. 12 shows that the chemiluminescent signal (RLU) was directly proportional (R=0.973) to the %GHb in the sample. Thus the assay accurately detects %GHb in both one-step and two-step formats.

Example 7
Use of Different Antibodies

Previous examples all use a DEAE-purified mouse monoclonal antibody (IgG$_1$) to human hemoglobin from Medix Biotech. Other antibodies, including polyclonal, from different species, and monoclonal, can also be used.

The GHb assay was performed as in Example 3. except both incubations were done at 37° C. for 10 minutes, with samples prepared as in Example 4.A., the microparticles from Example 1.A. and the following antibodies to human hemoglobin labeled with acridinium as in Example 2: (1) polyclonal goat anti-human hemoglobin (#CR8000 GAP, Cortex Biochem, San Leandro, Calif.), (2) monoclonal anti-human hemoglobin (#A36380, BiosPacific, Emeryville, Calif.), (3) polyclonal goat anti-human hemoglobin (#G32100, BiosPacific, Emeryville, Calif.), and (4) polyclonal rabbit anti-human hemoglobin (#A118, Dako Corp., Carpinteria, Calif.). Results, shown in FIGS. 13 through 16, indicate that the chemiluminescent signal (RLU) was directly proportional to the %GHb in the sample. The correlation coefficients (R values) for assays using each Ab were 0.982, 0.975, 0.946 and 0.869 respectively. Thus, polyclonal or monoclonal antibodies to human hemoglobin are useable in this assay format for accurately detecting %GHb.

While the invention has been described in each of its various embodiments, it is expected that certain modifications thereto may be effected by those skilled in the art without departing from the true spirit and scope of the invention as set forth in the specification and accompanying claims.

What is claimed is:

1. A one-read method of determining the percentage of glycated hemoglobin (GHb) in a whole blood sample without having to measure total hemoglobin (Hb), which comprises the steps of:
   a) lysing a whole blood sample to release hemoglobin;
   b) incubating said lysed blood sample with solid phase, said solid phase being coupled to a boronate affinity complex wherein said boronate affinity complex specifically captures glycated hemoglobin (GHb) in direct proportion to the percentage of glycated hemoglobin (GHb) in the sample and wherein a ratio of total hemoglobin (Hb) to boronate affinity complex is at least about 0.01;
   c) adding a labeled component specific for hemoglobin to said sample;
   d) measuring a resultant signal; and
   e) determining a percentage of glycated hemoglobin in the sample based on said resultant signal.

2. The method of claim 1, wherein said solid phase is selected from the group consisting of beads, microparticles, magnetic microparticles, microtiter plates and tubes.

3. The method of claim 1, wherein said boronate affinity complex contains a boronate moiety which is selected from the group consisting of boric acid, boronate compounds and phenylboronic acids.

4. The method of claim 3, wherein said phenylboronic acids are selected from the group consisting of 4-carboxyphenylboronic acid, 3-nitro-5-carboxyphenylboronic acid and m-aminophenylboronic acid (APBA).

5. The method of claim 1, wherein said labeled component is selected from the group consisting of labeled monoclonal and polyclonal antibodies, and other labeled molecules with an affinity for hemoglobin.

6. The method of claim 5, wherein said labeled component is a labeled monoclonal antibody.

7. The method of claim 1, wherein said labeled component is a label which is not linked to an antibody, said label being capable of generating a signal by specific binding to the hemoglobin in the absence of said antibody.

8. The method of claim 1, wherein a label of said labeled component is selected from the group consisting of radioactive, fluorescent, chemiluminescent and enzymatic substances.

9. A one-read method of determining the percentage of glycated hemoglobin (GHb) in a whole blood sample without having to measure total hemoglobin (Hb), which comprises the steps of:
   a) incubating a lysed whole blood sample with a solid phase, said solid phase being coupled to a boronate affinity complex, wherein said boronate affinity complex specifically captures glycated hemoglobin (GHb) in direct proportion to the percentage of glycated hemoglobin (GHb) in the sample and wherein a ratio of total hemoglobin (Hb) to boronate affinity complex is at least about 0.01;
   b) adding a labeled component specific for hemoglobin to said sample;
   c) measuring a resultant signal; and
   d) determining the percentage of glycated hemoglobin in said sample based on said resultant signal.

10. A one-read method of determining the percentage of glycated hemoglobin (GHb) in a whole blood sample without having to measure total hemoglobin (Hb), which comprises the steps of:
   a) lysing a whole blood sample to release hemoglobin;
   b) incubating said lysed blood sample with a solid phase, said solid phase being coupled to a boronate affinity complex, wherein said boronate affinity complex specifically captures glycated hemoglobin (GHb) in direct proportion to the percentage of glycated hemoglobin (GHb) in the sample and wherein a ratio of total hemoglobin (Hb) to boronate affinity complex is at least about 0.01;
   c) adding hydrogen peroxide to said sample;
   d) measuring a resultant signal generated by the peroxidase-like activity of the hemoglobin; and
   e) determining a percentage of glycated hemoglobin in the sample based on said resultant signal.

* * * * *